(12) United States Patent
Lee et al.

(10) Patent No.: US 9,226,938 B2
(45) Date of Patent: Jan. 5, 2016

(54) COMBINATORIAL THERAPY FOR TREATMENT OF OSTEOARTHRITIS OF THE KNEE

(71) Applicant: RMG Rehabilitation Management Group, LP, Houston, TX (US)

(72) Inventors: Mark Wayne Lee, Florence, SC (US); John Samuel Vick, St. Albans, MO (US)

(73) Assignee: RMG REHABILITATION MANAGEMENT GROUP, LP, Houston, TX (US)

( * ) Notice: Subject to any disclaimer, the term of this patent is extended or adjusted under 35 U.S.C. 154(b) by 246 days.

(21) Appl. No.: 13/958,292

(22) Filed: Aug. 2, 2013

(65) Prior Publication Data

US 2014/0276312 A1      Sep. 18, 2014

Related U.S. Application Data

(60) Provisional application No. 61/784,782, filed on Mar. 14, 2013.

(51) Int. Cl.
| | |
|---|---|
| *A61F 5/00* | (2006.01) |
| *A61K 31/728* | (2006.01) |
| *A61F 5/01* | (2006.01) |
| *A61B 5/00* | (2006.01) |
| *A61B 6/00* | (2006.01) |

(52) U.S. Cl.
CPC ............. *A61K 31/728* (2013.01); *A61F 5/0123* (2013.01); *A61B 5/4528* (2013.01); *A61B 5/4585* (2013.01); *A61B 6/487* (2013.01); *A61B 6/505* (2013.01); *A61B 2505/09* (2013.01)

(58) Field of Classification Search
CPC .................. A61F 2/30756; A61F 2002/30062; A61F 2002/30225; A61F 2002/30673; A61F 2002/30677; A61F 2002/30685; A61F 2002/30751; A61F 2002/30764; A61F 2002/30766; A61F 2002/30838; A61F 2002/30878; A61F 5/0123; A61L 27/20; A61L 27/18; A61L 27/26; A61L 2430/06; A61L 27/48; A61L 27/34; A61L 27/50; A61L 27/54; A61L 27/56; A61L 27/52; A61L 27/3834; A61L 2430/02; A61L 27/3817; A61L 27/3843; A61B 5/4528; A61B 2505/09; A61B 5/4585; A61B 6/487; A61B 6/505; A61K 31/728
USPC ........................................ 602/23–28; 128/882
See application file for complete search history.

(56) References Cited

U.S. PATENT DOCUMENTS

| | | | |
|---|---|---|---|
| 2008/0171968 A1* | 7/2008 | Stout et al. ...................... | 604/71 |
| 2009/0012615 A1* | 1/2009 | Fell ............................ | 623/14.12 |
| 2012/0165257 A1* | 6/2012 | Byers et al. .................... | 514/8.8 |

FOREIGN PATENT DOCUMENTS

WO      2012143876 A1      10/2012

OTHER PUBLICATIONS

Bliddal, Henning.; "Placement of Intra-Articular Injections Verified by Mini Air-Arthrography," Ann Rheum Dis 1999; 58:641-643.
Zhang, et al.; "OARSI Recommendations for the Management of the Hip and Knee Osteoarthritis, Part II: OARSI Evidence Based, Expert Consensus Guidelines," Osteoarthritis Research Society International; (2008) 16, 137-162; Elsevier Ltd.
International Search Report and Written Opinion for International Application No. PCT/US2014/027216 (USPT/0002PC) dated Jul. 29, 2014.

* cited by examiner

*Primary Examiner* — Michael Brown
(74) *Attorney, Agent, or Firm* — Patterson & Sheridan, LLP

(57) ABSTRACT

Embodiments of the present invention generally relate to methods of knee rehabilitation. Embodiments generally include the use of viscosupplementation delivered intra-articularly in conjunction with rehabilitative therapy and an unloading knee brace. The injection of the viscosupplementation is guided such that the entire dose is delivered to the joint and can flow tricompartmentally.

11 Claims, 4 Drawing Sheets

COMBINATORIAL THERAPY FOR TREATMENT OF OSTEOARTHRITIS OF THE KNEE

CROSS-REFERENCE TO RELATED APPLICATIONS

This application claims benefit of U.S. Provisional Patent Application Ser. No. 61/784,782, filed Mar. 14, 2013, which is incorporated herein by reference.

BACKGROUND OF THE INVENTION

1. Field of the Invention

Embodiments of the present invention generally relate to joint rehabilitation. More specifically, embodiments generally relate to methods of using a combination therapy including a viscosupplementation and physical therapy for joint rehabilitation in a patient.

2. Description of the Related Art

Knee osteoarthritis (OA) is among the most common causes of musculoskeletal pain and disability in the United States. Since there is no cure for OA at present, the primary aims of treatment are to reduce pain, maintain or improve function and mobility, and prevent or slow the progression of adverse changes to the joint tissues, while keeping potential therapeutic toxicities to a minimum. Current treatment guidelines begin with non-pharmacologic protocols, such as patient education, weight loss, and physical therapy.

Non-pharmacologic approaches frequently provide insufficient pain relief and restoration of function and mobility, and pharmacologic modalities become necessary. Although simple analgesics such as non-steroidal anti-inflammatory drugs (NSAIDs) provide relief for many OA patients with mild to moderate pain, alternatives should be considered for patients who fail to obtain adequate symptomatic relief with these measures. Although NSAIDs and/or cyclooxygenase 2 (COX-2) selective inhibitors are frequently effective for the relief of moderate to severe OA pain, these options are not always effective, and may be inappropriate in patients with gastrointestinal or cardiovascular risk factors. Furthermore, analgesics are designed to prevent the sensation of pain and thus will not prevent or delay further degradation of the joint.

For patients who do not get adequate pain relief from simple analgesics, like acetaminophen or from exercise and physical therapy, intra-articular injections of hyaluronate provide another treatment option to address symptomatic pain and delay the need for a total joint replacement surgery. It is known that the concentration of native hyaluronate is deficient in individuals suffering from OA and, therefore, joint injections of exogenous hyaluronate is believed to replenish these molecules and restore the viscoelastic properties of synovial fluid. It is this property that is responsible for lubricating and cushioning the joints. Independent of the mechanism of action, pain relief can be observed for about six months following a treatment course of hyaluronate. A treatment course for hyaluronate products on the US market can range from single injection product to others that require 3 to 5 once a week injections to attain this durability of pain relief.

However, as stated previously, pain relief does not solve the problem. Analgesics mitigate the pain but provide minimal benefit to stemming the progression of OA in the knee. Hyaluronate or physical therapy as currently provided also reduce pain to some extent, but overall degradation of the joint is not significantly affected. As such, there is a need in the art for better methods of treatment for OA.

SUMMARY OF THE INVENTION

Embodiments of the present invention generally relate to methods for use of hyaluronate and physical therapy for joint rehabilitation in OA patients. In one embodiment, a method of treatment for a joint can include determining a site of injection in a knee of a patient using flow determination imaging, injecting a volume of a medium to high molecular weight hyaluronate composition into the selected site of injection, wherein the high molecular weight hyaluronate composition flows tricompartmentally, providing one or more rehabilitation routines to the patient, wherein the rehabilitation routines increase blood flow and strengthen muscles proximate to the joint and supporting the knee using a weight bearing support at least during one of the one or more rehabilitation routines.

In another embodiment, a method for treating osteoarthritis in a patient can include providing an unloading knee brace for supporting a knee of a patient such that at least a portion of the weight born by the knee is supported by the brace, determining an injection site in the knee of the patient, the injection site selected to allow for tricompartmental flow, injecting a volume of a hyaluronate composition into the injection site with fluoroscopic guidance and providing one or more rehabilitative exercise sessions to the patient. The hyaluronate composition can include a high molecular weight hyaluronate and a diluent, wherein the volume of the diluent and the high molecular weight hyaluronate is greater than 2.0 ml, such as at least 2.5 ml. In another embodiment, a method for treatment of a joint can include determining whether tricompartmental flow exists in an affected knee joint of a patient, affixing a weight bearing support to the affected knee joint of the patient, wherein the affected knee joint has one or more degeneration sites, if tricompartmental flow exists, determining one or more sites of injection in the affected knee joint which allow tricompartmental flow and are proximate to one or more degeneration sites in the affected knee joint, wherein the sites of injection are determined using flow determination imaging, injecting a hyaluronate composition comprising hyaluronate with a molecular weight of greater than 500 kD, such as greater than 700 kD, into the one or more sites of injection using fluoroscopic guidance, the injection delivered from three to five times with a separation between injections of seven to ten days and providing one or more physical therapy rehabilitative routines to the patient before each injection, the routines designed to strengthen a muscle group which reduces pressure on at least one of the one or more degeneration sites.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Embodiments described herein generally relate to joint rehabilitation using combinatorial therapy. By combining rehabilitation therapy with a targeted large volume injection of a medium to high molecular weight viscosupplementation, such as hyaluronate, into a space which allows for tricompartmental flow, the viscosupplementation can be delivered to all three compartments of the joint. The benefits here include decreased pain both during and after rehabilitation therapy, better proprioception during and after rehabilitation therapy, and increased anti-inflammatory response both in OA damaged compartments of the knee and compartments which may not yet be affected. By decreasing the inflammatory response, reducing pain and increasing stability, the patient is more capable of performing physical therapy. Further, reduced pain and increased non-stressed mobility in the joint increases patient compliance with rehabilitation, thus providing synergistic results. These benefits can be further enhanced by an unloading or weight bearing knee brace, thus supporting the joint during movement. The invention disclosed herein can be more clearly understood with reference to the figures described below which illustrate embodiments of the invention.

Figure 1:
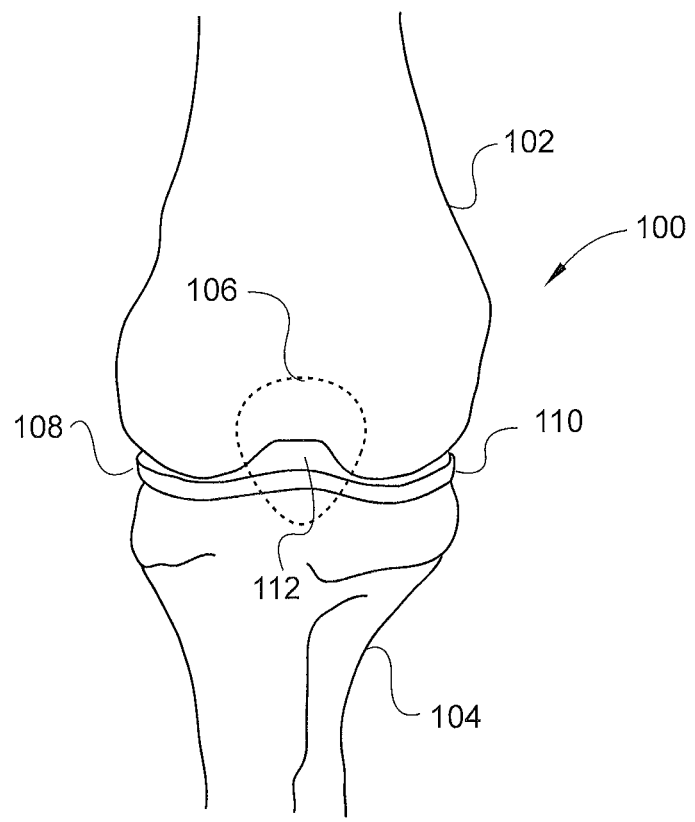
FIG. 1 depicts a right knee joint showing three compartments.

FIG. 1 is a frontal view of a knee joint 100 depicting the three compartments. In this depiction, a femur 102, a tibia 104 and a patella 106 are shown forming the knee joint 100. The femur 102 has two distinct protrusions at its lower (distal) end, known as the lateral condyle and the medial condyle. These protrusions provide two weight bearing surfaces between the tibia 104 and the femur 102. The space between the weight bearing surface on the outer side of the knee 100 is a first compartment 108, which corresponds to the lateral femoro-tibial compartment. The space between the weight bearing surface on the inner side of the knee 100 is a second compartment 110, which corresponds to the medial femoro-tibial compartment. A third compartment 112 is in the center of the knee, formed between the patella 106 and the space between the lateral and medial condyle of the femur 102, which corresponds with the patellofemoral compartment.

In a normal knee joint 100, the first compartment 108, the second compartment 110 and the third compartment 112 include synovial fluid, including endogenous hyaluronate, articular cartilage and the medial and lateral meniscus that help protect the weight bearing surfaces of the femur 102 and the tibia 104 during movement. Hyaluronate is a glycosaminoglycan (GAG), and in particular hyaluronate is an unbranched polysaccharide made up of alternating glucuronic acid and N-acetyl glucosamine units. It is a viscoelastic material that is also found in the extracellular matrix of cartilage attached to collagen. In particular, hyaluronate is an important building component of aggregated proteoglycans which impart resilient characteristics of articular cartilage.

However, in OA, the articular cartilage of the first compartment 108, the second compartment 110, the third compartment 112 or combinations thereof degrades, at least in part, by gradual loss of its extracellular matrix (ECM), which is composed, at least in part, of aggrecan and type II collagen. Loss of large proteoglycan aggrecan decreases cartilage compressive stiffness and precedes the damage to collagen fibrillar network, which is responsible for tensile properties of the tissue. This progressive degradation decreases the separation between the weight bearing surfaces and causes pain in the knee joint 100. Hyaluronate can provide several important functions in synovial fluid. First, it is a lubricant that reduces the friction and increases spacing between the femur and the tibia. Second, it inhibits certain enzymes that break down articular cartilage in the joints. Third, it acts as an anti-inflammatory agent within the joint. Fourth, it inhibits pain. By cushioning and lubricating the joints while maintaining the elasticity of the cartilage, hyaluronate helps maintain the spacing between the femur 102, the tibia 104 and the patella 106. Hyaluronate can thus be used in combination with rehabilitative therapy to treat disorders of the joints, such as OA of the knee.

Figure 2:
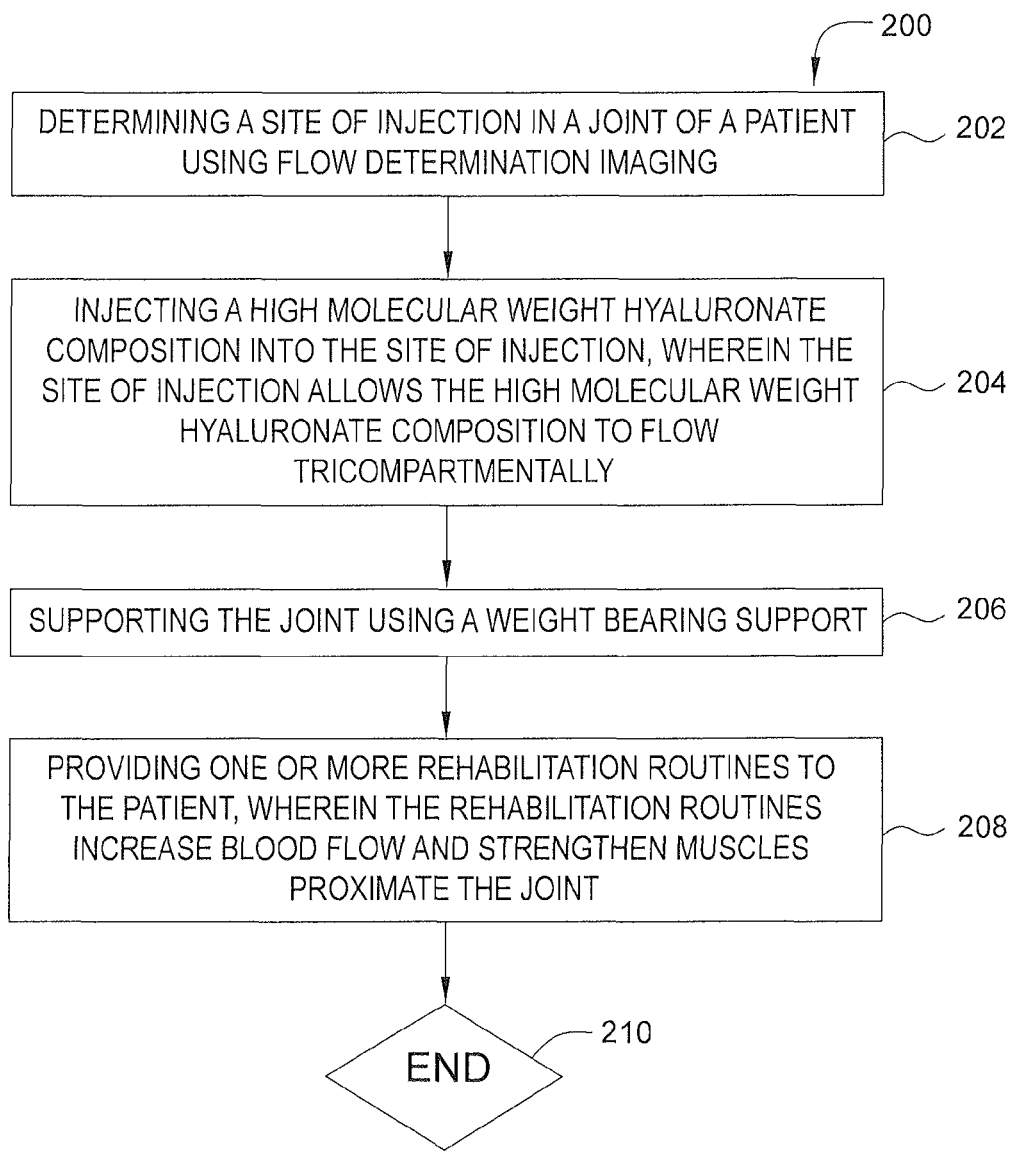
FIG. 2 is a block diagram of a method for joint rehabilitation according to one embodiment.

FIG. 2 is a block diagram of a method 200 for joint rehabilitation according to one embodiment. The method 200 begins by determining a "site of injection" of a patient using flow determination imaging, as in step 202. The flow determination imaging used in embodiments herein can be an arthrogram, as described herein. Initially, a contrast medium is injected into the intra-articular space. A fluoroscope can be used to provide guidance in injecting the contrast medium. The contrast medium comprises a substance which will not be detrimental to the affected knee while simultaneously allowing the internal, non-bone components of the knee to be visualized by arthrogram. Examples of contrast mediums used in one or more embodiments can include iodinated contrast agents such as, iopamidol or ioxaglate meglumine.

Once the contrast medium is injected, the affected knee joint can then be analyzed by arthrogram. The arthrogram can be performed using means known in the art, such as an x-ray machine. For example, a C-arm fluoroscopic machine can be used to perform the arthrogram after injection of the contrast medium. The arthrogram employs a series of x-rays of the joint with the contrast medium to acquire a three dimensional view of the joint. In one or more embodiments, the arthrogram is taken from anterior (front) to posterior (back) and laterally, such that a full three dimensional view is shown. Based on the visualization of the intra-articular compartments, one or more sites of injection can be determined such that the injection can flow tricompartmentally. Arthrograms used in one or more embodiments herein can be taken either in a flexed or extended knee position to determine positions that will allow tricompartmental flow in the flexed position, the extended position or both. Other means of determining a point of injection which allows for tricompartmental flow in a knee joint may be used without diverging from embodiments described herein. Though the above description focuses on the use of arthrograms to determine tricompartmental flow, any known flow determination imaging can be used. Other flow determination imaging techniques or apparatus may be used without diverging from the inventive aspects described here. For example, tricompartmental flow may be determined by arthrography or by injecting a radiolabeled metabolite.

Current practice in OA treatment for intra-articular injection is to inject a viscosupplementation on the lateral side without determination of a site of injection. This is believed to result in incomplete injection of the viscosupplementation and subsequent partial injection into soft tissue (such as fat pads or ligaments) or misplacement of the entire injection into the soft tissue. Either of these events can create a pseudoseptic response in the patient. Pseudosepsis is a noninfectious disorder that mimics sepsis. Symptoms of pseudosepsis can include fever/leukocytosis, hypotension, severe joint inflammation/pain and effusion (collection of fluid in the surrounding tissue). Therefore, it is important to maintain proper intra-articular injection both for patient wellbeing and for proper rehabilitation of the affected knee. Proper placement of the intra-articular injection allows complete delivery of the hyaluronate composition to the affected and surrounding compartments. Complete delivery of the hyaluronate composition provides better cushioning for the compartments of the joint, thus allowing increased mobility and decreased inflammation in the affected knee.

The method 200 further includes injecting a medium to high molecular weight hyaluronate composition into the site of injection. The site of injection is selected to allow the medium to high molecular weight hyaluronate composition to flow tricompartmentally, as in step 204. Using the arthrogram analysis described above, a specific injection site can be selected. At this point, the hyaluronate composition including a high molecular weight hyaluronate is then injected into the intra-articular space. In this instance, medium to high molecular weight hyaluronate means hyaluronate with a molecular weight of greater than or equal to 500 kilo Daltons (kD). In one embodiment, the molecular weight can be between 500 kD to 10000 kD, such as between 500 kD to 6000 kD. In another embodiment, the molecular weight can be from 500 kD to 1700 kD, such as from 600 kD to 1100 kD. In further embodiments, the molecular weight can be greater than 700 kD, such as greater than 800 kD, greater than 900 kD or greater than 1000 kD. The hyaluronate can be a native form of hyaluronate or a conjugated form of hyaluronate. Further, the hyaluronate compositions used in the embodiments described herein may be entirely a specific weight, a specific weight range (such as from 700 kD to 1000 kD) or a combination of weight ranges. For example, the hyaluronate compositions may include from 0.4% to 0.8% w/v hyaluronate, wherein the hyaluronate includes both from 0.3% to 0.5% w/v of between 600 kD to 1100 kD hyaluronate and from 0.1% to 0.5% w/v of a low molecular weight hyaluronate (less than 600 kD) dissolved in a 0.9%-1.0% (physiological) saline solution. Examples of hyaluronate compositions which can be used in embodiments of the invention include SUPARTZ® available from Bioventus LLC located in Durham, N.C.

Without intending to be bound by theory, it is believed that the medium to high molecular weight hyaluronate provides a synergistic benefit in combination with physical therapy which both reduces the progression of OA and increases the pain reduction benefit. First, the medium to high molecular weight hyaluronate is a longer chain molecule which is believed to decrease the rate of molecular degradation and increase the residence time of the molecule in the knee. The increased residence time provides an increased reduction of pain over lower weight compositions. As described previously, hyaluronate is an unbranched polysaccharide made up of alternating glucuronic acid and N-acetyl glucosamine units. As the hyaluronate breaks down into a smaller chain molecule, viscosupplementation properties decrease and the monomers can eventually be removed from the joint by normal metabolism. The longer chain hyaluronate molecule is believed to require more metabolism prior to removal from the body, due at least in part to steric hindrance from multiple proteins binding at sites along the unbranched chain. Since metabolism is inhibited by the longer chain, the residence time, and thus the physiological benefits, of the hyaluronate is believed to be increased.

Second, the high molecular weight hyaluronate degrades to a lower molecular weight hyaluronate, thus increasing the half-life for pharmaceutical-like properties of hyaluronate. Hyaluronate has been observed to create an anti-inflammatory response when delivered properly to the intra-articular space of the knee. One possible route of pharmacological activity may be through binding to the CD44 receptor. CD44 is involved both in degradation of hyaluronate, cell adhesion, lymphocyte activation/mobilization and hematopoiesis. It is believed that by introducing a medium to high molecular weight hyaluronate, degradation of the existing/endogenous hyaluronate is slowed by the aforementioned enzymatic mechanism of breaking down a higher molecular weight hyaluronate into a lower molecular weight hyaluronate, thus increasing the longevity of the pharmacological activity that accompanies the physical properties of hyaluronate. Further, it is believed that the presence of hyaluronate in the tricompartmental space leads to the production of endogenous hyaluronate. As such, the benefits of tricompartmental hyaluronate injection are self perpetuating.

The injection can be delivered as a single injection at a single site or multiple injections at a single or multiple sites. The injections need not deliver equal quantities of the hyaluronate composition. The hyaluronate composition can further include inert components, such as a diluent. The hyaluronate may be reconstituted or diluted in a diluent such as a saline solution. The diluent serves to increase the overall volume of the hyaluronate and act as a vehicle for delivery of the hyaluronate into the intra-articular area of the joint. The overall volume for the injection can be at least 2.0 ml. In one embodiment, the overall volume for the injection is between 2.0 and 2.5 ml. In another embodiment, the overall volume for the injection is greater than 2.5 ml It is believed to be important to increase the overall volume of the hyaluronate composition based on the degeneration of the joint, the size of the joint and the body dynamics of the person receiving the hyaluronate injections.

The method 200 can further include supporting the joint using a weight bearing support, as in step 206. Due to the nature of their osteoarthritis, many patients will suffer pain from arthritic compressive forces and have additional ligamentous instability. In conjunction with hyaluronate injections and physical therapy, patients with moderate to severe osteoarthritis may benefit from the use of a weight bearing supports, such as an off the shelf or custom fitted unicompartmental unloading knee brace, to reduce pain and provide stability. These braces or other weight bearing supports have the ability to decompress or shift compressive knee joint forces from the degenerative area to healthy compartments in the knee. They can also provide ligamentous stability anterior/posterior and/or medial/laterally through structural support and local perception. Additionally, the weight bearing support can allow for increased activity which can provide pain relief through sensory stimulation. In one embodiment, the unloading knee bracing is designed to put three points of pressure on the femur. These points of pressure are believed to force the knee to bend away from the painful aspect of the knee. Stated another way, it transfers or "unloads" stress or pressure from a degenerated portion of the knee to a less-degenerated or healthy portion of the knee.

Before or after the patient has received a hyaluronate injection, the patient can then be fitted for and receive the weight bearing support, such as the unicompartmental unloading knee brace. There are a number of braces that allow for unloading of the knee joint on the market. The joint support provided by the weight bearing support can be either continuous or periodic, based on the needs of the patient. Continuous can be defined as use of the weight bearing support at least 90% of the ambulatory time for the patient. Ambulatory time is defined as the time which the patient is alert. For example, a patient who is using a weight bearing support continuously may affix the weight bearing support upon waking up and remove the weight bearing support upon going to sleep. Any amount of time of use of the weight bearing support which is less than continuous, as defined above, is periodic. Stated another way, periodic is use of the weight bearing support for less than 90% of the ambulatory time. For example, a patient who is using a weight bearing support periodically may affix the weight bearing support prior to using the joint and remove the weight bearing support during any non-active time.

Without intending to be bound by theory, it is believed that unloading the knee joint during rehabilitative therapy is beneficial to both pain reduction and reduced progression of OA. By reducing the compression on the compartments of the knee, the patient will experience reduced pain, thus allowing the patient to move the joint more freely. Further, the decreased weight on the compartments of the knee will increase flow of the hyaluronate composition tricompartmentally. This both equilibrates the hydrostatic pressure in the intra-articular space of the knee and allows for delivery of the hyaluronate composition to both OA affected areas of the knee and areas not yet showing degeneration.

The method 200 further provides one or more rehabilitation routines to the patient, as in step 208. The six to eight week physical therapy and rehabilitation program consists of therapeutic exercises and education designed to increase blood flow and strengthen muscles proximate to the joint. The therapeutic exercises can also improve overall physical function and reduce pain both at the joint and in related areas of the body.

The physical therapy algorithm is medically necessary, measurable, and functionally based towards addressing activities of daily living (ADLs) and comparing prior functional levels to current functional levels. The algorithm challenges the patient on multiple physiological levels, such as strength, cardiovascular, balance/proprioception and coordination. One to five therapy visits can be scheduled prior to the first injection to allow for baseline functional testing.

Figure 3:
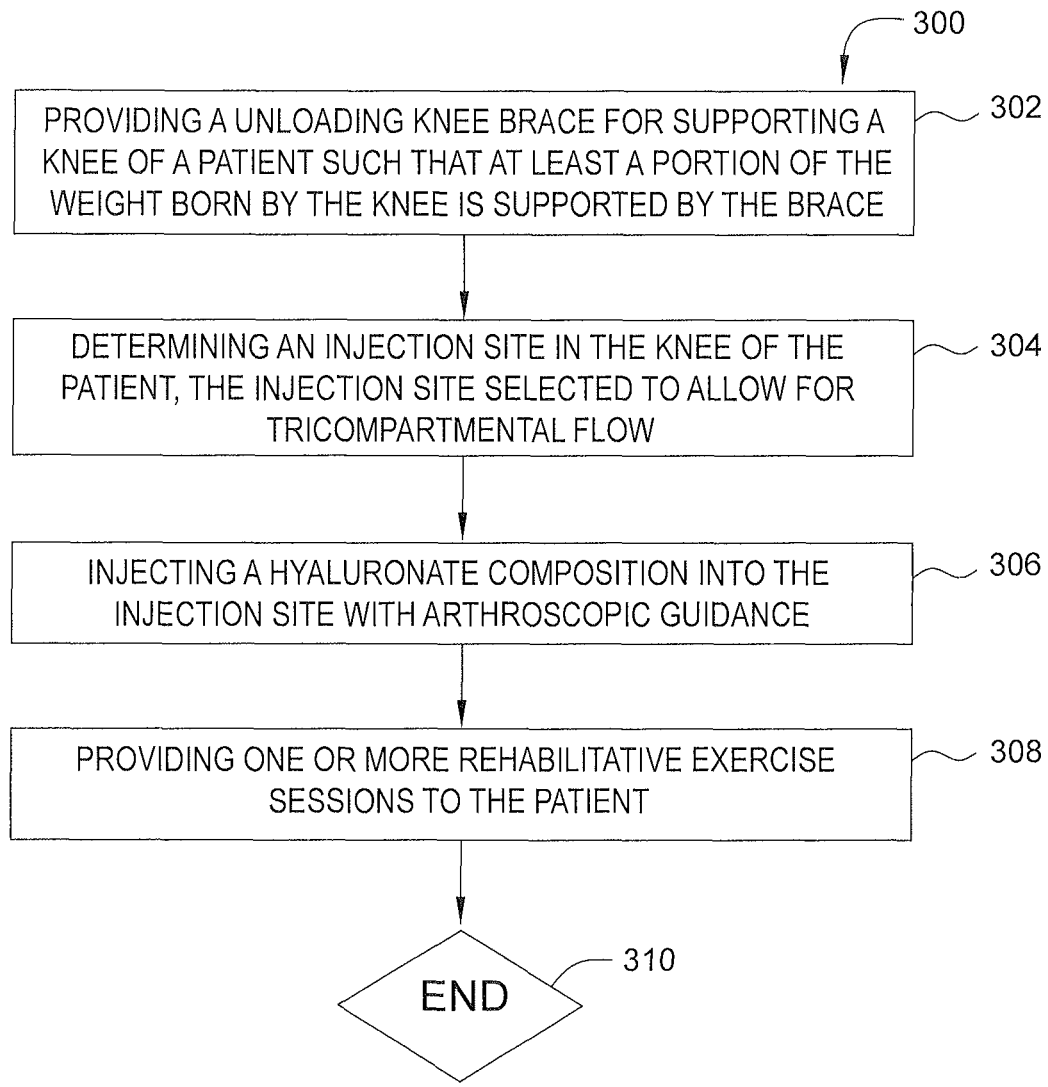
FIG. 3 is a block diagram of a method for combinatorial therapy including hyaluronate and rehabilitative therapy according to one embodiment.

FIG. 3 is a block diagram of a method for combinatorial therapy including hyaluronate and rehabilitative therapy according to another embodiment. The method 300 includes providing an unloading knee brace for supporting a knee of a patient such that at least a portion of the weight born by the knee is supported by the brace, as in step 302. In this embodiment, an unloading knee brace is provided to the patient to increase intra-articular flow. In one or more forms of OA, tricompartmental flow may be blocked or inhibited by degeneration of the knee at one or more compartments. By unloading the knee, tricompartmental flow can be temporarily reestablished, thus allowing for further rehabilitation.

Generally speaking, some patients do not have tricompartmental flow due to physiological anomalies, degeneration from OA progression, inflammation or for other reasons. The lack of tricompartmental flow prevents the injection of the complete volume of the hyaluronate into the intra-articular space which both reduces the efficacy of the hyaluronate and increases the likelihood of the injection flowing into the soft tissue. As such, these patients generally do not receive the full benefit of hyaluronate injection and rehabilitative therapy. By artificially increasing the tricompartmental flow using an unloading knee brace, these issues can be partially or completely remedied, allowing a larger patient population to benefit from the methods described herein.

The method 300 further includes determining an injection site in the knee for the patient. The injection site is selected to allow for tricompartmental flow, as in step 304. As described with reference to FIG. 2, the one or more injection sites can be determined by flow determination imaging, such as an arthrogram. The injection sites are initially determined based on tricompartmental flow. As a secondary consideration, sites that are closer to at least one of the degeneration sites are preferable to other sites.

The method 300 further includes injecting a hyaluronate composition into the injection site, as in step 306. The hyaluronate composition can include a high molecular weight hyaluronate and a diluent. The volume of the high molecular weight hyaluronate and the diluent can be at least 2.0 ml. As described above, greater volumes can be used with consideration of co-morbidities of the patient or patient-specific physiological differences. For example, the volume of the hyaluronate composition can be increased for a patient with a larger than normal knee joint or for an obese patient.

On the day of injections, the hyaluronate injections should be done following rehabilitative therapy. Rehabilitative therapy can be performed three times a week. The rehabilitative therapy can act synergistically with the hyaluronate by increasing the mobility of the hyaluronate composition across the three compartments. Injections can be done once every five to ten days, such as once every seven to ten days. The injections should be given between three and five times, such as a total of five injections. In embodiments where three injections of hyaluronate are used, injections can be given every ten days.

The method 300 further includes providing one or more rehabilitative exercise sessions prescribed to the patient, as in step 308. The rehabilitative therapy sessions generally begin with medical evaluation, followed by the exercise regimen. Rehabilitation therapy can be given three to five times a week over a period of six to eight weeks. In some embodiments, rehabilitation is given over a period of eight weeks at three times per week.

Figure 4:
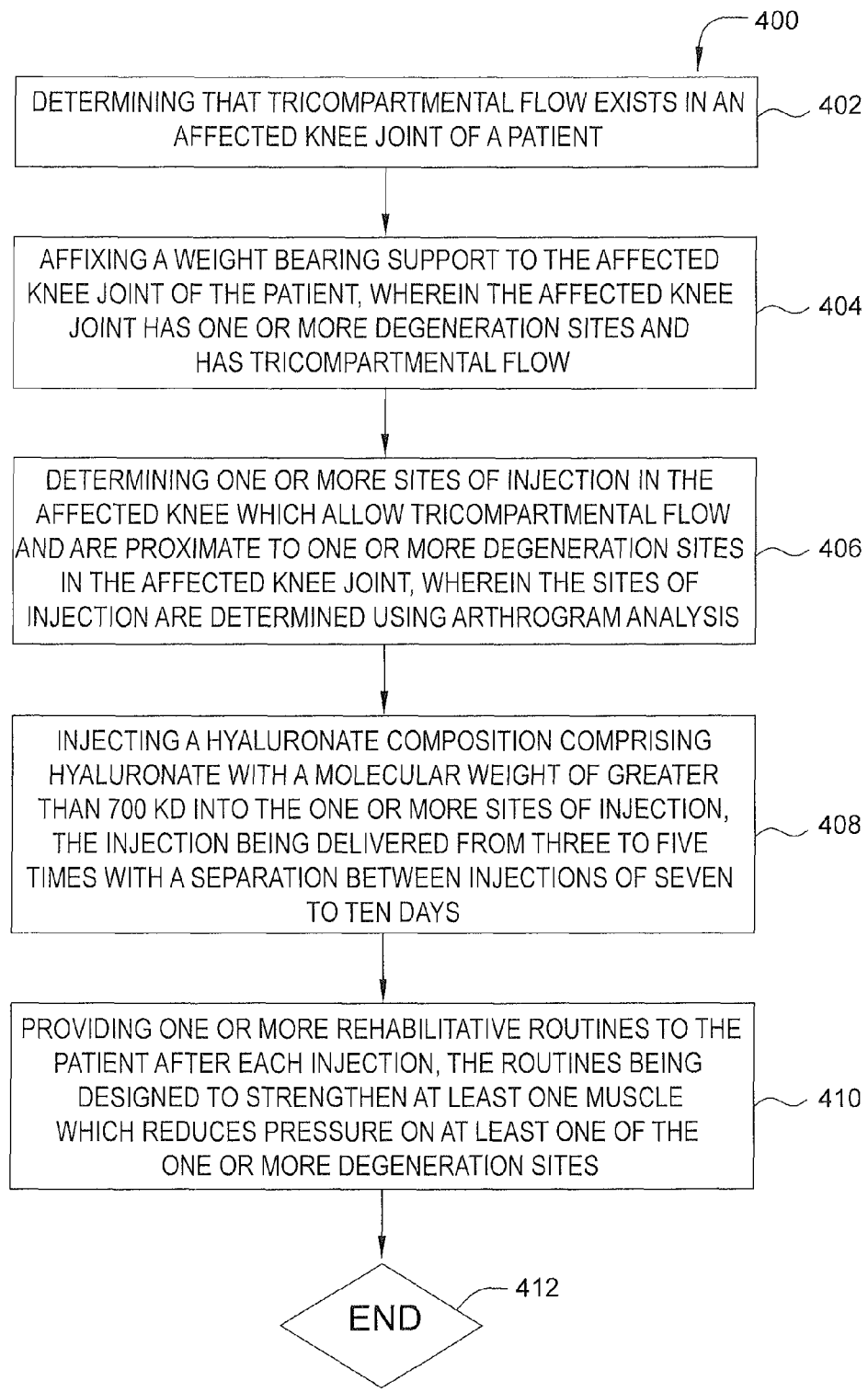
FIG. 4 is a block diagram of a method for combinatorial therapy including hyaluronate and rehabilitative therapy according to another embodiment.

FIG. 4 is a block diagram of a method for combinatorial therapy including hyaluronate and rehabilitative therapy according to another embodiment. The method 400 includes determining that tricompartmental flow exists in an affected knee joint of a patient, as in step 402. The arthrogram or other flow determination imaging can be performed as described with reference to FIGS. 2 and 3.

A patient who does not have tricompartmental flow in the affected knee joint, even with assistance, generally receives a less substantial benefit from this intervention than a patient who does have tricompartmental flow. By determining whether a patient has tricompartmental flow prior to beginning any intervention, the level of benefit received can be determined and steps can be taken to increase the benefit received. For example, in one embodiment the patient can be determined to have limited tricompartmental flow. The patient in this embodiment, may be fitted with a weight bearing support and reevaluated for tricompartmental flow after a period of time, such as two weeks. Further, this analysis can determine if there are contraindications to performing subsequent steps. Contraindications can include other joint issues like meniscal tears, anterior cruciate ligament (ACL) injury, posterior cruciate ligament (PCL) injury or other injuries that affect the patient's ability to receive the above treatment.

The method 400 can further include affixing a weight bearing support to the affected knee joint of the patient, wherein the affected knee joint has one or more degeneration sites, as in step 404. The weight bearing support used with embodiments herein can include those described with reference to FIGS. 2 and 3. As described above, the weight bearing support can be used to increase tricompartmental flow. However, the weight bearing support provides benefit to both a patient either with or without tricompartmental flow.

When a patient has a degenerative disorder, the patient can enter into what is colloquially known as a "degenerative cycle". As people develop OA either from injury and hereditary causes, the knee senses the injury and enzymes are released in to the knee to fight the injury. These enzymes, known as hyaluronidases break down hyaluronate and cartilage starting a downward spiral. As OA progresses there is less and less hyaluronate within the knee and OA related joint degeneration progresses faster. As expected, degeneration of the joint causes pain in the patient. This pain causes the patient to minimize movement and pressure on the joint. The movement, which would normally assist the flow of various healing factors (such as cytokines, leukocytes, endogenous opioids, blood vessel growth factors and the like) into and around the joint, is no longer present, which both slows down healing and increases nociception. The slowed healing leads to increased degeneration and increased pain in the joint as well as atrophy of the surrounding muscles, thus perpetuating the degenerative cycle. By lifting weight from the joint and increasing tricompartmental flow in the joint in combination with other interventions such as hyaluronate, this cycle can be slowed and/or reversed.

The method 400 can further include determining one or more sites of injection in the affected knee which allow tricompartmental flow and are proximate to one or more degeneration sites in the affected knee joint, wherein the sites of injection are determined using flow determination imaging, as in step 406. By using flow determination imaging, such as through an arthrogram, to determine both tricompartmental flow and a proper site of injection, the hyaluronate composition can be injected into the joint with a high degree of medical certainty (approaching 100%), while injecting the entire volume.

Without intending to be bound by theory, it is believed that the volume of the hyaluronate delivered is important to the overall success of the intervention. Degeneration in OA is generally marked with loss of cartilage, decreased production of synovial fluid, ECM degeneration of the contacting portions of the bone and aberrant immune response. As the joint (both bone and space between) degenerates, pain increases and the bones are allowed to make more contact. Injecting a volume into the joint in a space which allows for tricompartmental flow creates increased spacing and a consistant hydrostatic pressure across the joint. A larger volume injected within a range of tolerance creates a more natural separation between the bones and allows for more uniform delivery of the hyaluronate composition injected into the space. The more uniform delivery both increases lubrication locally in the compartment and allows for better receptor binding on type B synovial fibroblasts, which are located in the linings of the knee joints. Binding of hyaluronate to the receptors creates a positive feedback loop and, through one or more signal transduction pathways, the fibroblasts can then generate endogenous hyaluronate. This is believed to both reduce pain, reverse the catabolic pathways and provide for better overall outcomes.

The method 400 further includes injecting a hyaluronate composition comprising hyaluronate with a molecular weight of greater than 700 kD into the one or more sites of injection with fluoroscopic guidance. The injection can be delivered from three to five times with a separation between injections of seven to ten days, as in step 408. The high molecular weight hyaluronate can be delivered as a single intra-articular injection at the site of injection once every seven to ten days. The injection can be given three to five times over the course of a six to eight week rehabilitation session. If fewer injections are given, the time between injections should be increased, to increase the benefit received and allow for the optimum number of physical therapy exercise sessions.

Without intending to be bound by theory, hyaluronate can be considered both a device and a pharmaceutical. As with most pharmaceuticals, the dose given is designed to create a therapeutic level of the drug in the compartment. Factors affecting the therapeutic level of the drug include compartmentalization and drug metabolism. The treatment regimen of hyaluronate is designed to be given once a week over a period of five weeks. Based on half-life of the drug, most patients will receive direct benefit from the five injections of hyaluronate for a period of five weeks. Some patients, however, may require fewer injections to maintain appropriate levels of hyaluronate and/or appropriate volume of fluid in the joint. These patients may receive as few as three injections. Since the goal of the injections is to maintain a specific amount of the composition in the tricompartmental space over the six to eight week course of rehabilitation, fewer injections should be extended over a longer period of time with the intent to maintain the therapeutic level of the hyaluronate during the course of the rehabilitation therapy.

The method 400 further includes providing one or more rehabilitative routines to the patient after each injection. The routines are preferably designed to strengthen at least one muscle which reduces pressure on at least one of the one or more degeneration sites, as in step 410. Reducing pressure on the knee joint and strengthening the surrounding muscles is important to the overall success of the therapy. By increasing muscle growth, not only do you reduce pressure on the joint but you increase vascularization of the surrounding tissue.

CONCLUSION

Embodiments described herein relate to methods of rehabilitating a knee joint. As of 2005, OA affects approximately 13.9% of the U.S. population over the age of 25, and this proportion is steadily increasing. There is no known cure for OA, thus patients rely largely on various interventions to both improve outcomes and quality of life. Embodiments described herein disclose methods of combinatorial therapy which improves patient recovery and quality of life over previously known techniques or methods. By incorporating an injection of a medium to high molecular weight hyaluronate composition injected intra-articularly at a position which has been determined to allow for tricompartmental flow while simultaneously providing targeted rehabilitative exercises, patients receive a significantly better outcome than other treatments which are available. The benefits of the above combinatorial therapy can be further enhanced by the periodic or consistent use of a weight bearing support.

While the foregoing is directed to embodiments of the present invention, other and further embodiments of the invention may be devised without departing from the basic scope thereof, and the scope thereof is determined by the claims that follow.

What is claimed is:
1. A method for treating osteoarthritis in a patient comprising:
providing an unloading knee brace for supporting a knee of a patient such that at least a portion of the weight born by the knee is supported by the brace;

determining an injection site in the knee of the patient, the injection site selected to allow for tricompartmental flow;

injecting a volume of a hyaluronate composition into the injection site with fluoroscopic guidance, the hyaluronate composition comprising:
- a high molecular weight hyaluronate; and
- a diluent, wherein the volume of the diluent and the high molecular weight hyaluronate is at least 2.5 ml; and providing one or more rehabilitative exercise sessions to the patient.

2. The method of claim 1, wherein the high molecular weight hyaluronate is a non-conjugated hyaluronate.

3. The method of claim 1, wherein the high molecular weight hyaluronate has a molecular weight between 600 kD to 1100 kD.

4. The method of claim 3, wherein the hyaluronate composition comprises from 0.3% to 0.5% w/v of high molecular weight hyaluronate.

5. The method of claim 1, wherein the rehabilitative exercise sessions occur three to five times a week at the clinic (and utilizing a home exercise program) over a period of six to eight weeks.

6. The method of claim 5, wherein the hyaluronate composition is injected starting on week 1 or week 2.

7. The method of claim 1, wherein the determination of the injection site comprises an arthrogram, the arthrogram taken at least from anterior to posterior.

8. The method claim 1, wherein the hyaluronate injection is given once a week for a period of three to five weeks and are given prior to the rehabilitative exercise sessions for the same week.

9. A method for treatment of a joint comprising:
determining whether tricompartmental flow exists in an affected knee joint of a patient;
affixing a weight bearing support to the affected knee joint of the patient, wherein the affected knee joint has one or more degeneration sites;
if tricompartmental flow exists, determining one or more sites of injection in the affected knee joint which allow tricompartmental flow and are proximate to one or more degeneration sites in the affected knee joint, wherein the sites of injection are determined using flow determination imaging;
injecting a hyaluronate composition comprising hyaluronate with a molecular weight of greater than 700 kD into the one or more sites of injection using fluoroscopic guidance, the injection delivered from three to five times with a separation between injections of seven to ten days; and
providing one or more physical therapy rehabilitative routines to the patient before each injection, the routines designed to strengthen a muscle group which reduces pressure on at least one of the one or more degeneration sites.

10. The method of claim 9, wherein the hyaluronate composition has a volume of at least 2.5 ml.

11. A method for treating osteoarthritis in a patient comprising:
providing an unloading knee brace for supporting a knee of a patient such that at least a portion of the weight born by the knee is supported by the brace;
determining an injection site in the knee of the patient, the injection site selected to allow for tricompartmental flow;
injecting a volume of a hyaluronate composition into the injection site with fluoroscopic guidance, the hyaluronate composition comprising:
- a high molecular weight hyaluronate; and
- a diluent, wherein the volume of the hyaluronate composition is at least 2.5 ml; and providing one or more rehabilitative exercise sessions to the patient.

* * * * *